(12) United States Patent
Lee et al.

(10) Patent No.: US 9,207,178 B2
(45) Date of Patent: Dec. 8, 2015

(54) DOUBLE-LIGHT CABINET FOR BIOLOGICAL TEST

(71) Applicant: SMOBIO Technology, Inc., Hsinchu (TW)

(72) Inventors: Kuan-Lin Lee, Hsinchu (TW); Chen-Sheng Wu, Hsinchu (TW); Chun-Hsien Kuo, Hsinchu (TW)

(73) Assignee: SMOBIO Technology, Inc., Hsinchu (TW)

( * ) Notice: Subject to any disclaimer, the term of this patent is extended or adjusted under 35 U.S.C. 154(b) by 519 days.

(21) Appl. No.: 13/630,046

(22) Filed: Sep. 28, 2012

(65) Prior Publication Data
US 2013/0083190 A1 Apr. 4, 2013

(30) Foreign Application Priority Data
Sep. 30, 2011 (TW) ............................... 100135633 A (51) Int. Cl.
*G01N 21/64* (2006.01)
(52) U.S. Cl.
CPC ...... *G01N 21/645* (2013.01); *G01N 2021/6417* (2013.01); *G01N 2021/6471* (2013.01); *G01N 2201/0627* (2013.01); *G01N 2201/0634* (2013.01)

(58) Field of Classification Search
USPC ................................ 250/504 R, 458.1, 461.1
See application file for complete search history.

(56) References Cited

U.S. PATENT DOCUMENTS

| 5,847,507 A | * | 12/1998 | Butterworth et al. | .......... 313/512 |
| 2003/0230728 A1 | * | 12/2003 | Dai et al. | .................... 250/458.1 |
| 2006/0030026 A1 | * | 2/2006 | Garcia | ....................... 435/287.1 |

* cited by examiner

*Primary Examiner* — Paul Hyun
(74) *Attorney, Agent, or Firm* — Hannah M. Tien (57) ABSTRACT

A double-light cabinet for testing a biological sample labeled with fluorochrome includes a case, in which a light unit and a diffusion unit are received. The light unit has two spot light sources to emit spot lights with specified wavelengths according to the test, and the diffusion unit diffuses the spot lights into surface lights, to which that the biological sample is exposed. The present invention further includes an amber filter unit to filter the surface light to enhance the signal of biological samples. Using the lights with specified wavelengths, the present invention may serve both functions of excitation and illumination of the biological sample.

23 Claims, 14 Drawing Sheets

DOUBLE-LIGHT CABINET FOR BIOLOGICAL TEST

The current application claims a foreign priority to the patent application of Taiwan No. 100135633 filed on Sep. 30, 2011.

BACKGROUND OF THE INVENTION

1. Field of the Invention

The present invention relates generally to a test system, and more particularly to a double-light cabinet for biological test.

2. Description of the Related Art

With advancement in biotechnology, we pay much attention to test the biological sample. In prior art, the biological sample is tested by fluorescence detection. In fluorescence detection, fluorochrome has an excitation state and an emission state to mark the specified molecules in the biological sample.

In fluorescence detection, it must select a light source with a specified wavelength, according to the fluorochrome that the fluorochrome will be excited by the light to generate specific fluorescence for the biological test.

In prior art, UV light is taken as the light source to excite the fluorochrome. However, UV light must be operated in a dark room. Besides, it is known that UV light is harmful to human skin. It is bad for the researches who are exposed to the UV light for a long time in the test.

In conclusion, the present invention will introduce a double-light cabinet for biological test which can solve the problems in association with known prior arts.

SUMMARY OF THE INVENTION

The primary objective of the present invention is to provide a double-light cabinet for biological test, which provides lights with different wavelengths to excite and illuminate the biological sample.

Another objective of the present invention is to provide a double-light cabinet, which provides a plurality of LEDs to emit lights with different wavelengths, and the light is diffused by a diffusion unit to transform the separated spot lights into a stable and uniform surface light.

Another objective of the present invention is to provide a double-light cabinet, which the light unit is coated with blue dye and fitted with a blue filter member to obtain a good result of the biological test.

Another objective of the present invention is to provide a double-light cabinet, which provides a light unit and a diffusion unit to form a backlight module to reduce the size.

Another objective of the present invention is to provide a double-light cabinet, which compares the background image and the biological sample image to form a detection image for user to observe.

According to the objectives of the present invention, the present invention provides a double-light cabinet for testing a biological sample added with fluorochrome, including a case, a light unit, and a diffusion unit. The case has a chamber. The light unit is provided in the chamber of the case and has first light sources to emit a first light with a first wavelength and second light sources to emit a second light with a second wavelength. The first light excites the fluorochrome, and the second light illuminates the biological sample. The diffusion unit is received in the chamber of the case, on which the biological sample is put. The first light and the second light emit to the diffusion unit to form a first surface light and a second surface light to emit to the biological sample to excite the fluorochrome to generate a third light with a third wavelength.

In comparison with the prior art, the present invention provides a plurality of spot light sources, such as blue light source and white light source, for excitation and luminance in the test. The spot light sources, such as blue light source, may be filtered by filter unit, such as the blue filter member, to transform the light of the spot light source into a light with almost single wavelength. The spot lights may be diffused by the diffusion unit to form a surface light, so that the biological sample on the diffusion unit may be exposed under a smooth and uniform surface light for test. In addition, according to the arrangement of the light source and the diffusion unit, it may be classified into direct-light type, side-light type, and edge-light type. The edge-light type may reduce the size of the cabinet, and the side-light type may operate without the filter member. In other words, in order to overcome the color difference of the spot light sources, except for the side-light type, the spot light sources of the direct-light type and the edge-light type must be filtered by the filter member.

The present invention further provides the amber filter unit to receive the surface light and filter it that may obtain a good result of test. Besides, the present invention may catch the images before the test and after the test to find the difference and adjust the brightness, white balance, and contrast of the images that the researcher may easily observe the biological sample.

DETAILED DESCRIPTION OF THE INVENTION

Figure 1:
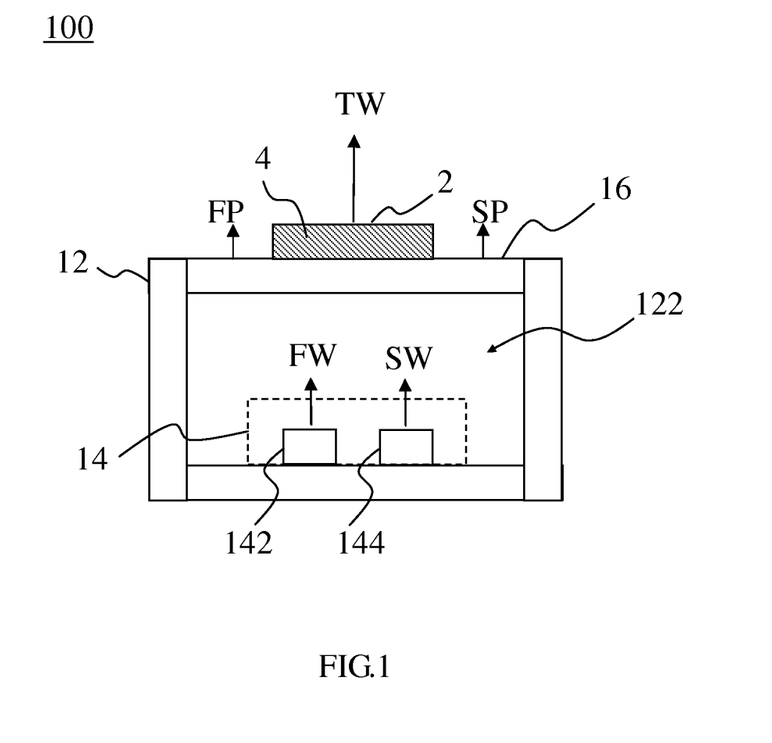
FIG. 1 is a sectional view of the double-light cabinet of a first preferred embodiment of the present invention.

As shown in FIG. 1, a double-light cabinet 10 for biological test of the first preferred embodiment of the present invention is to test a biological sample 2 labeled with fluorochrome 4. The biological sample 2 may be gel electrophoresis of deoxyribonucleic acid (DNA), protein, or any bio-materials.

The double-light cabinet 10 includes a case 12, a light unit 14, and a diffusion unit 16. The case 12 forms a chamber 122 therein.

The light unit 14 is provided in the chamber 122 of the case 12, including a plurality of first light sources 142 and second light sources 144. The first light sources 142 emit a first light FW with a first wavelength, and the second light sources 144 emit a second light SW with a second wavelength. The first light FW excites the fluorochrome 4, and the fluorochrome 4 emits a third light TW with a third wavelength after excitation. The second light SW may illuminate the biological sample 2.

The first light source 142 has a plurality of blue LEDs (light emitting diode) that the first light FW is blue light which is visible light with a wavelength in a range between 445 nm and 575 nm. In the present invention, the first wavelength is a constant in a wavelength range of blue-green light. The second light SW is white light, and the wavelength thereof may be a combination of several wavelengths, such as a combination of two lights (blue and yellow) or three lights (blue, green, and red), or inorganic UV light source added with blue, green, or red phosphors.

The first wavelength of the first light FW of the first light source 142 is in association with the fluorochrome 4 to change the band gap of the fluorochrome 4 and generate the third light TW while the fluorochrome 4 is exposed to the first light source 142.

Figure 2:
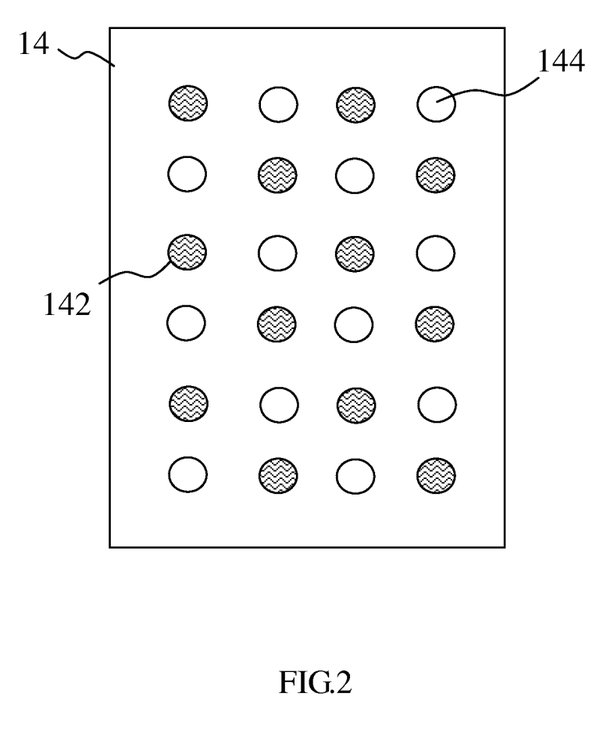
FIG. 2 is a sketch diagram of the first preferred embodiment of the present invention, showing the arrangement of the first light sources and the second light sources.

The first light sources 142 and the second light sources 144 may be provided in an alternate arrangement as shown in FIG. 2.

The diffusion unit 16 is provided in the chamber 122, on which the biological sample 2 is put. The first light sources 142 and the second light sources 144 are under the diffusion unit 16 to emit the first light FW and the second light SW to the diffusion unit 16. The diffusion unit 16 diffuses the first light FW and the second light SW to form a first surface light FP with the first wavelength and a second surface light SP with the second wavelength. The biological sample 2 is exposed to the first surface light FP and the second surface light SP. The first surface light FP may excite the fluorochrome 4 to generate the third light TW. In other words, the diffusion unit 16 transforms the first and the second lights FW, SW of spot light into the first and the second surface light FP, SP of uniform surface light. In an embodiment, the diffusion unit is a ground glass plate or an acrylic plate.

In the present invention, the light unit 14 is set at a bottom side of the diffusion unit 16. Thus, the first light FW and the second light SW may directly enter the diffusion unit 16, so called direct-light backlight module.

Figure 3:
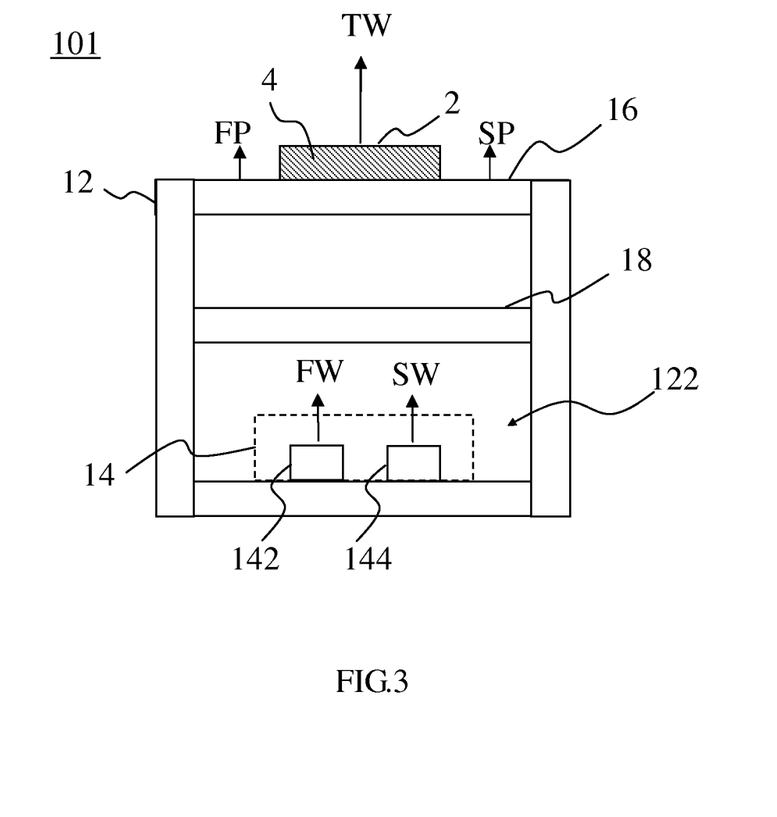
FIG. 3 is a sectional view of the double-light cabinet of a second preferred embodiment of the present invention.
Figure 4:
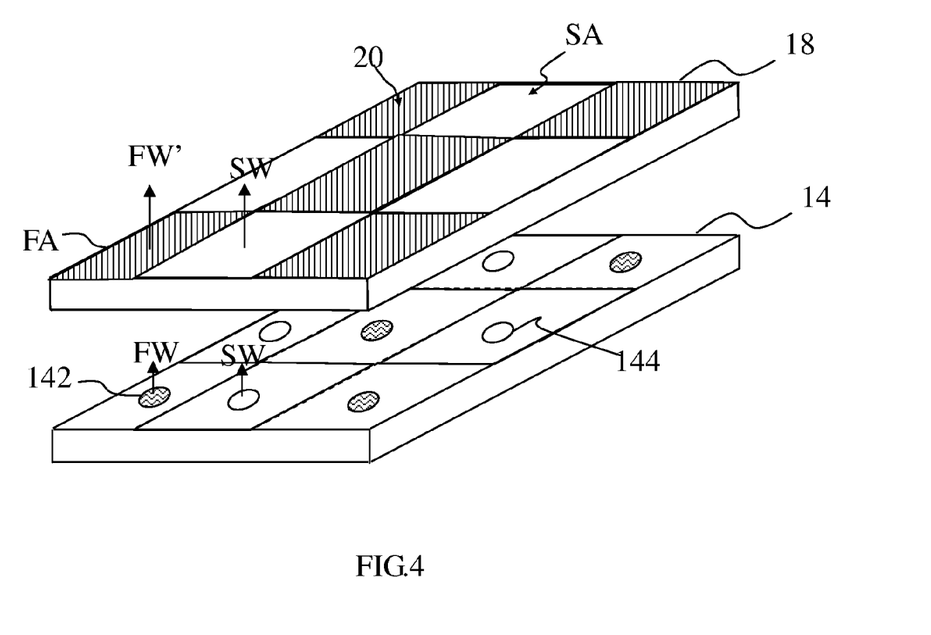
FIG. 4 to FIG. 6 show three arrangements of the filter unit, the first light sources, and the second light sources of FIG. 3.

FIG. 3 shows a double-light cabinet 101 for biological test of the second preferred embodiment of the present invention, including the case 12, the light unit 14, and the diffusion unit 16, as well as a filter unit 18. The filter unit 18 has a plurality of first areas FA and second areas SA, as shown in FIG. 4. The first light sources 142 and the second light sources 144 are set at a bottom side of the filter unit 18 with the first light sources 142 facing the first areas FA and the second light sources 144 facing the second areas SA.

The sizes of the first and the second areas FA, SA are respectively identical to the sizes or spot sizes of the first and the second light sources 142, 144. They may be defined by the manufacturer according to the process also.

In the present embodiment, the first light sources 142 are blue LEDs, and the second light sources 144 are white LEDs, and the blue LEDs are under the first areas FA and the white LEDs are under the second areas SA, respectively.

In an embodiment, as shown in FIG. 4, the first light FA of the filter unit 18 is coated with dye 20, such as blue dye. The first light FW (the blue light of the blue LEDs) is filtered in the first areas FA and transformed into a single first light FW' with a single wavelength. And then, the single first light FW' will be emitted to the diffusion unit 16. In comparison the first light FW with the single first light FW', most wavelengths of the first light FW are filtered out by the filter unit 18, and a specified wavelength may pass the filter unit 18 to form the single first light FW'. In addition, the second areas SA may be transparent, so that the second light SW directly passes through the filter unit 18 and emits to the diffusion unit 16.

Figure 5:
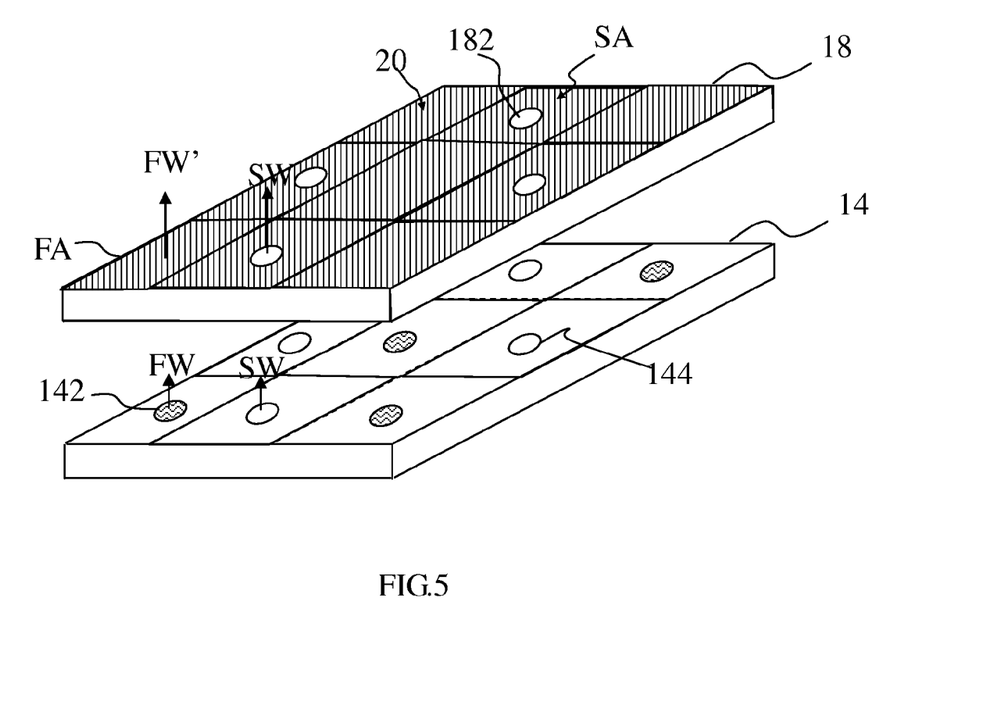

In an embodiment, as shown in FIG. 5, the entire filter unit 18, including the first area FA and the second areas SA, is coated with the dye 20, and is provided with openings 182 on the second areas SA. The second light sources 144 emit the second light SW to the diffusion unit 16 through the openings 182 without filtering, and the first light FW of the first light sources 142 is filtered by the filter unit 18 to form the single first light FW'.

Figure 6:
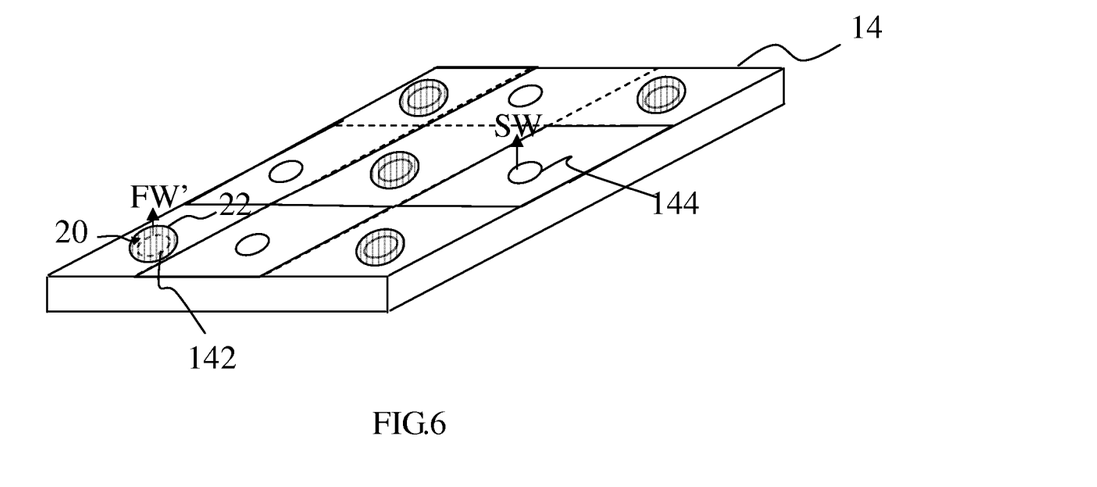

In an embodiment, as shown in FIG. 6, the filter unit 18 has a plurality of filter members 22, which are coated with the dye 20, covering the first light sources 142, respectively. The filter members 22 may transform the first light FW into the single first light FW'. The same as above, the second areas SA are transparent, so that the second light SW of the second light sources 144 directly passes through the filter unit 18 and emits to the diffusion unit 16.

For example, the dye 20 is blue while the first light sources 142 are blue LEDs to generate blue light with single wavelength.

Figure 7:
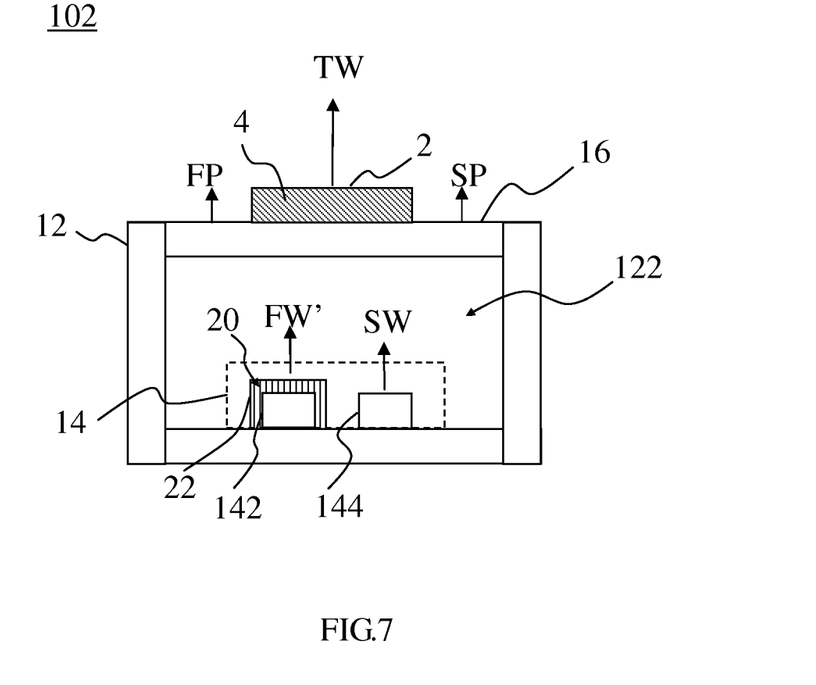
FIG. 7 is a sectional view of the double-light cabinet of a third preferred embodiment of the present invention.
Figure 8:
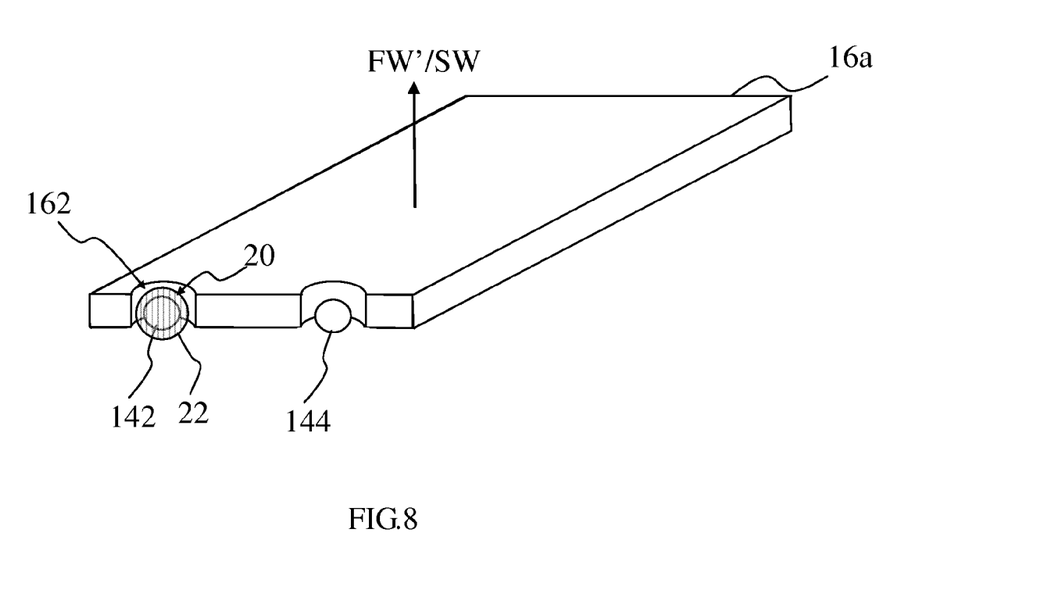
FIG. 8 is a sketch diagram of the diffusion unit of a fourth preferred embodiment of the present invention.

FIG. 7 shows a double-light cabinet 102 for biological test of the third preferred embodiment of the present invention, which is similar to the second preferred embodiment, except that the double-light cabinet 102 may be operated without the filter unit 18. The first light sources 142 are embedded in the filter members 22 to form the single first light FW'. Besides, the arrangement of the first and the second light sources 142, 144 may be as same as that is shown in FIG. 2. FIG. 8 shows a diffusion unit 16a of the fourth preferred embodiment of the present invention, which has a plurality of recesses 162 on an edge thereof to receive the first light sources 142 and the second light sources 144 therein.

Figure 9:
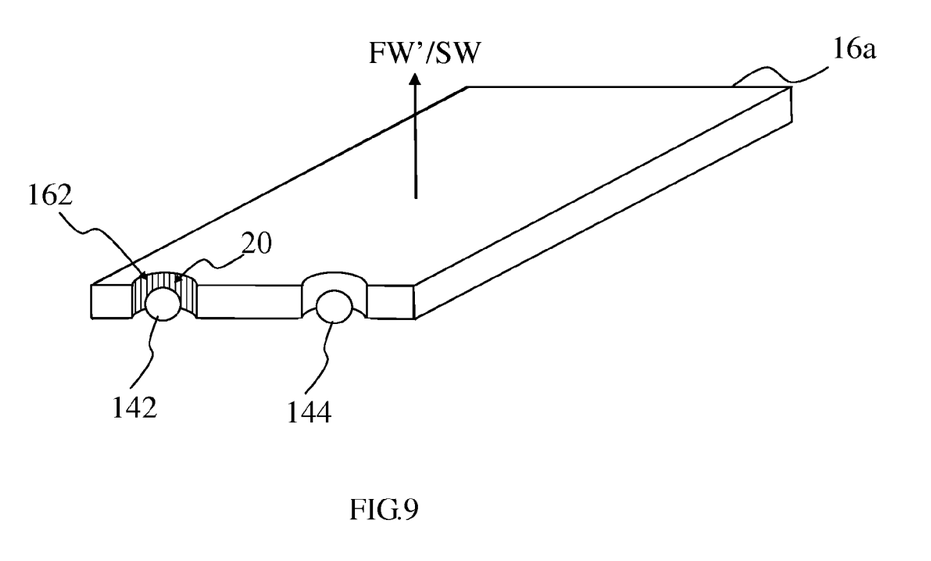
FIG. 9 shows a sketch diagram of the recesses of FIG. 8.

The first light sources 142 may be embedded in the filter members 22 as described above. It may also be coated with the dye 20 on a sidewall of the recess 162 receiving the first light sources 142, as shown in FIG. 9. These procedures may make the first light sources 142 emit the single first light FW' with the single wavelength.

For example, the dye 20 is blue while the first light sources 142 are blue LEDs to generate blue light with single wavelength.

Figure 10:
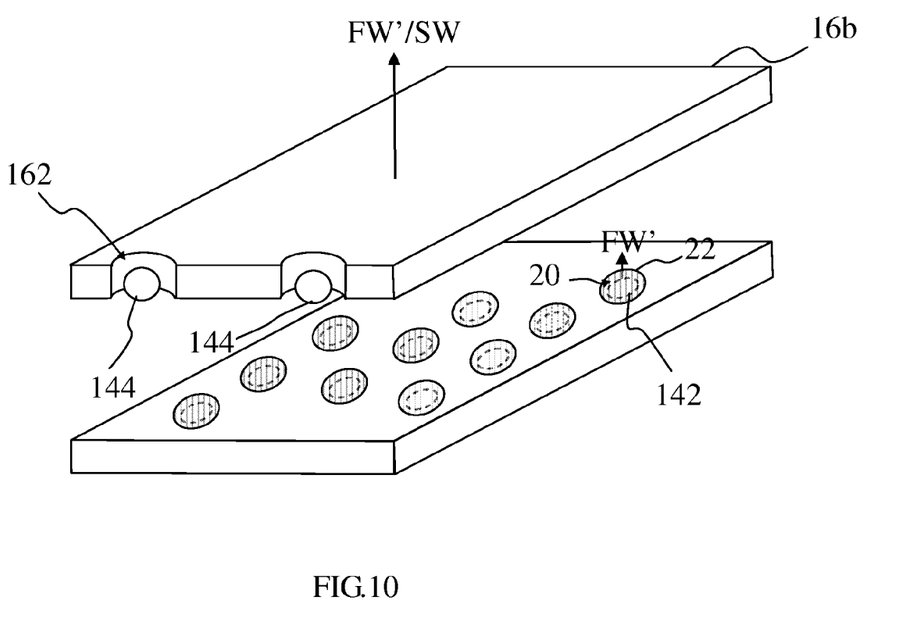
FIG. 10 is a sectional view of the double-light cabinet of a fifth preferred embodiment of the present invention.
Figure 11:
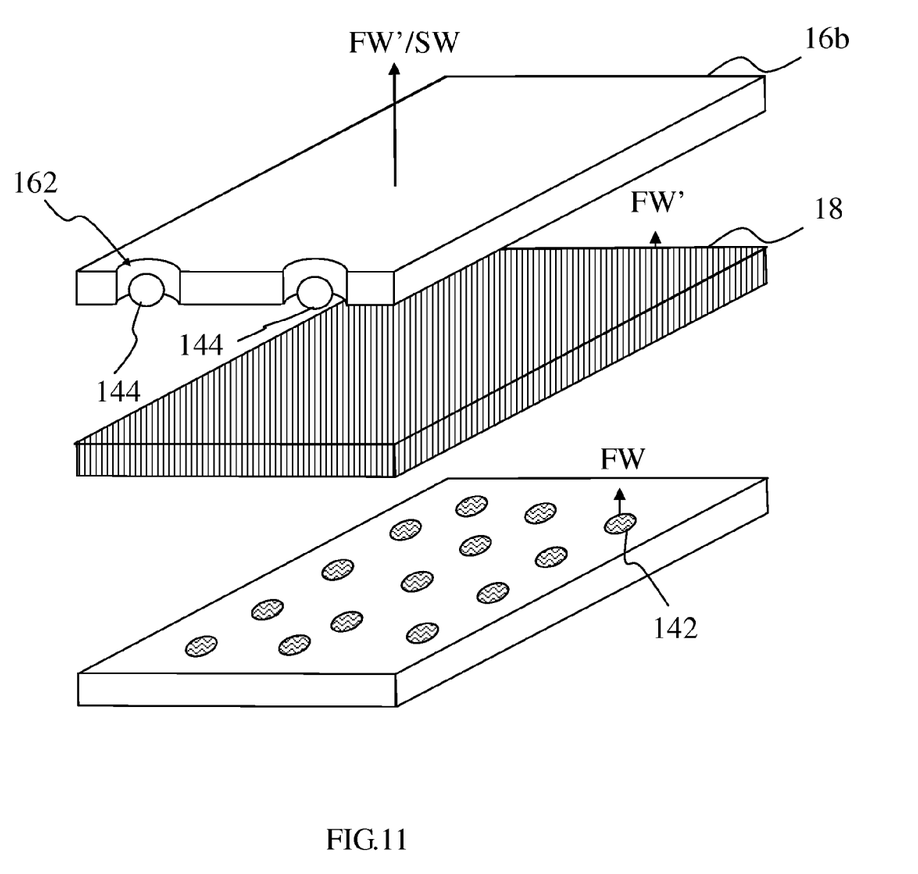
FIG. 11 is a sketch diagram of the diffusion unit of FIG. 10.

FIG. 10 shows a diffusion unit 16b of the fifth preferred embodiment of the present invention, which has a plurality of recesses 162 on an edge thereof to receive the second light sources 144 therein. The first light sources 142 are under the diffusion unit 16b. The first light sources 142 may be embedded in the filter members 22, or they may be covered by the filter member 22 (FIG. 11) to make the first light source 142 emit the single first light FW' with the single wavelength to the diffusion unit 16b. The filter unit 18 is between the first light sources 142 and the diffusion unit 16b.

Figure 12:
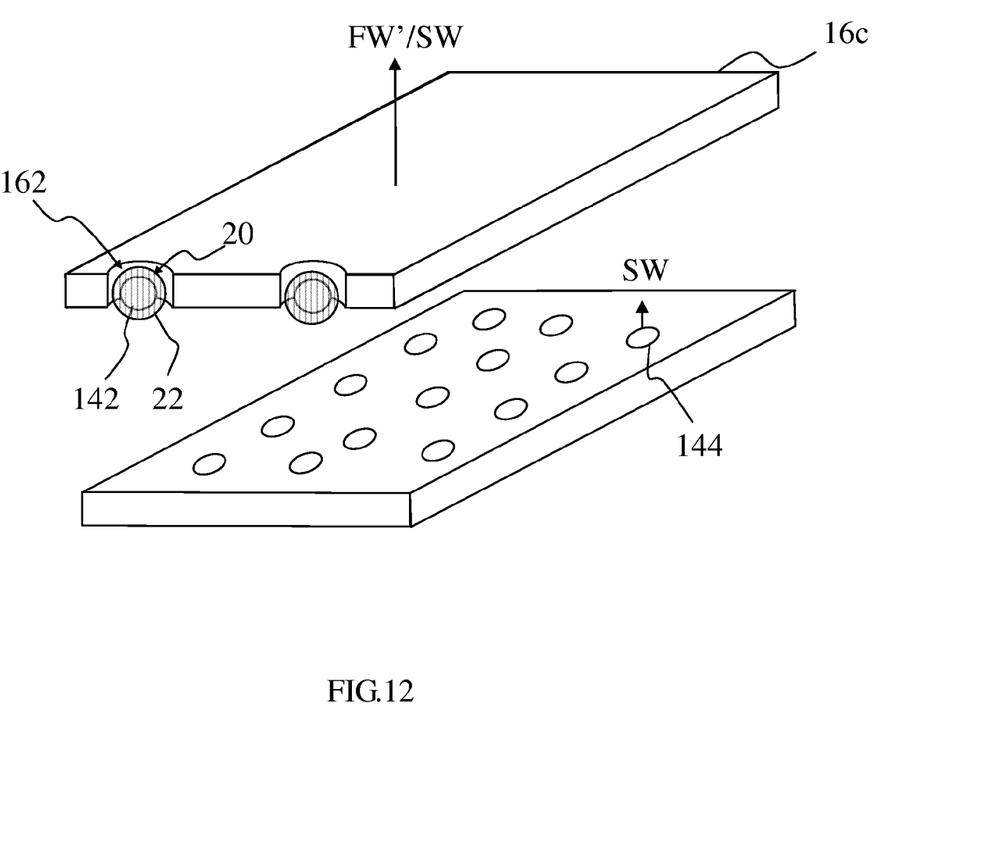
FIG. 12 is a sectional view of the double-light cabinet of a sixth preferred embodiment of the present invention.

FIG. 12 shows a diffusion unit 16c of the sixth preferred embodiment of the present invention, which is opposite to the structure as shown in FIG. 10. The first light sources 142 are mounted in the recess 162 of the diffusion unit 16c, and the second light sources 144 are under the diffusion unit 16b.

The first light sources 142 may be embedded in the filter members 22, or it may be coated with the dye 20 on sidewall of the recesses 162 to make the first light sources 142 emit the single first light FW' with the single wavelength.

For example, the dye 20 is blue while the first light sources 142 are blue LEDs to generate blue light with single wavelength.

Figure 13:
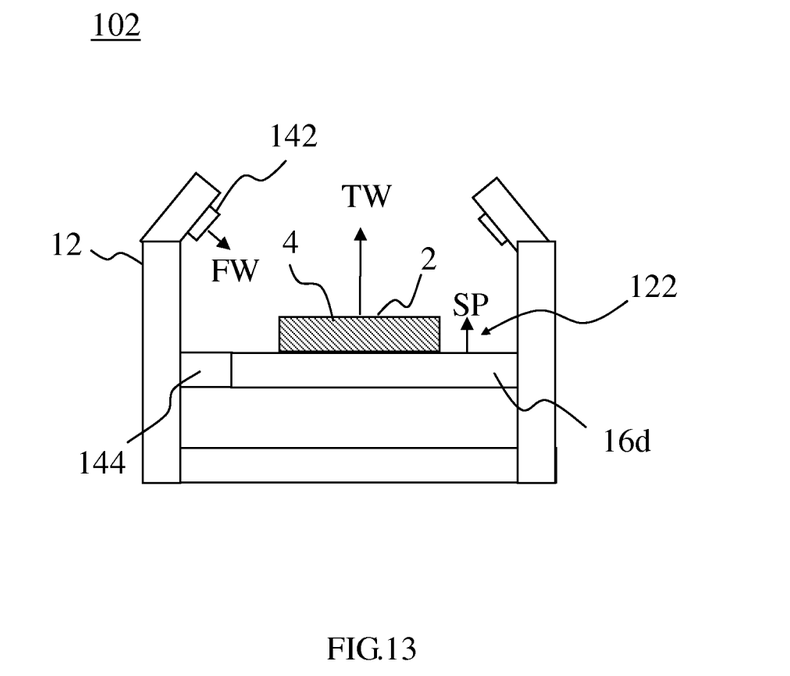
FIG. 13 is a sectional view of the double-light cabinet of a seventh preferred embodiment of the present invention.

FIG. 13 shows a double-light cabinet 102 for biological test of the seventh preferred embodiment of the present invention, which includes a diffusion unit 16d with recesses on an edge thereof to receive the second light source 144 therein. The first light sources 142 are above the diffusion unit 16d to directly emit the first light FW to the biological sample 2 on the diffusion unit 16d in a direction diverging from a normal of the diffusion unit 16d. In the present embodiment, no filter member or filter unit is needed to filter the first light FW because the first light sources 142 emit the first light FW directly to the biological sample 2. Therefore, the first light FW may excite the fluorochrome 4 in the biological sample 2 without any problem.

Figure 14:
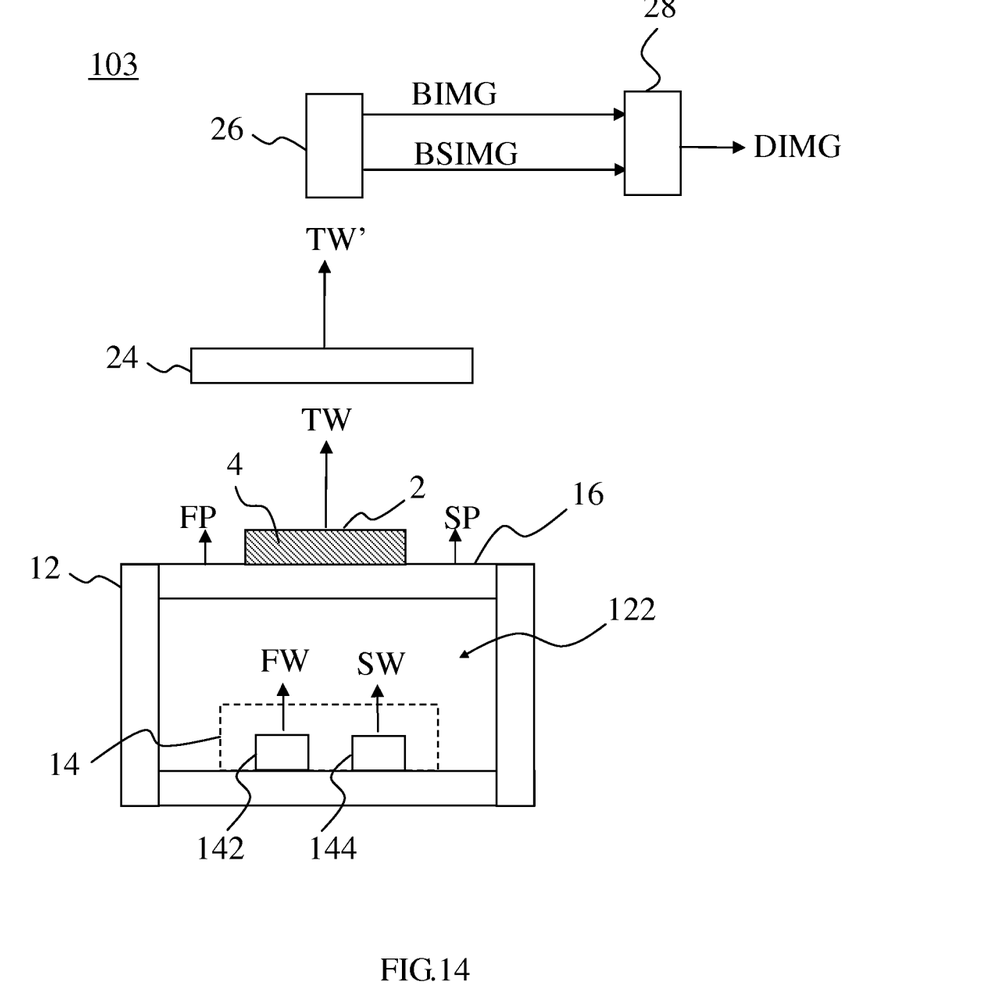
FIG. 14 is a sectional view of the double-light cabinet of an eighth preferred embodiment of the present invention.

FIG. 13 shows a double-light cabinet 103 for biological test of the eighth preferred embodiment of the present invention including the case 12, the light unit 14, and the diffusion unit 16, as well as an amber filter unit 24 above the diffusion unit 16. The amber filter unit 24 may receive the third light TW and filter the noise out to form a clear third light TW'. The clear third light TW' may enhance the excitation of the fluorochrome 4 to obtain a good result of test.

The double-light cabinet 103 further includes an image capture unit 26 above the amber filter unit 24 to catch image through the amber filter unit 24. The images includes a background image BIMG and a biological sample image BSIMG. The BIMG is taken when the biological sample 2 is not put on the diffusion unit 16 yet, and the biological sample image BSIMG is taken when the biological sample 2 is put on the diffusion unit 16. A comparison unit 28 is connected to the image capture unit 26 to compare the biological sample image BSIMG with the background image BIMG, and forms a detection image DIMG according to the comparison. The detection image DIMG shows the difference between the biological sample image BSIMG and the background image BIMG. The detection image DIMG may show the difference of brightness, white balance, or contrast.

The double-light cabinet of the present invention provides a plurality of spot light sources, such as blue light sources and white light sources, for excitation and illumination. The spot light sources, such as blue light sources, may be filtered by filter unit, such as the blue filter members, to transform the light of the spot light source into a light with almost single wavelength. The spot lights may be diffused by the diffusion unit to form a surface light, so that the biological sample on the diffusion unit may be exposed to a smooth and uniform surface light for test. In addition, according to the arrangement of the light sources and the diffusion unit, it may be classified into direct-light type, side-light type, and edge-light type. The edge-light type may reduce the size of the cabinet, and the side-light type may be operated without the filter unit. In other words, in order to overcome the color difference of the spot light sources, except for the side-light type, the spot light sources of the direct-light type and the edge-light type must be filtered by the filter members.

The present invention further provides the amber filter unit to filter the surface light in order to obtain a good result of test. Besides, the present invention may catch the images before the test and after the test to find the difference and adjust the brightness, white balance, and contrast of the images. Hence, the researcher may clearly observe the biological sample.

The description above is a few preferred embodiments of the present invention and the equivalence of the present invention is still in the scope of claim construction of the present invention.

What is claimed is:

1. A double-light cabinet for testing a biological sample labeled with fluorochrome, comprising:
    a case having a chamber;
    a light unit, which is provided in the chamber of the case, having first light sources to emit a first light with a first wavelength and second light sources to emit a second light with a second wavelength, wherein the first light excites the fluorochrome, and the second light illuminates the biological sample;
    a diffusion unit received in the chamber of the case, wherein the first light and the second light emit to the diffusion unit to form a first surface light and a second surface light and emit to the biological sample to excite the fluorochrome to generate a third light with a third wavelength; and
    a filter unit comprising a plurality of first areas and second areas, wherein the first light sources and the second light sources are under the diffusion unit in an arrangement of the first light sources respectively facing the first areas and the second light sources respectively facing the second areas;
    wherein the diffusion unit is a ground glass plate or an acrylic plate;
    wherein the first areas of the filter unit are coated with dye that the first light emits to the diffusion unit through the first areas, and the second areas are transparent so that the second light emits to the diffusion unit through the second areas.

2. The double-light cabinet as defined in claim 1, wherein the first wavelength of the first light is in a range between 445 nm and 575 nm.

3. The double-light cabinet as defined in claim 1, wherein the second light of the second light sources is white light.

4. The double-light cabinet as defined in claim 3, wherein the first light sources include a plurality of blue LEDs and the second light sources include a plurality of white LEDs.

5. The double-light cabinet as defined in claim 4, further comprising a plurality of filter members respectively covering the first light sources.

6. The double-light cabinet as defined in claim 1, wherein the filter unit has openings on the second areas, through which second light emits to the diffusion unit.

7. The double-light cabinet as defined in claim 1, further comprising an amber filter unit above the diffusion unit to filter the third light.

8. The double-light cabinet as defined in claim 7, further comprising an image capture unit above the amber filter unit to catch images through the amber filter unit, wherein the images include a background image which is taken when the biological sample is not put on the diffusion unit yet, and a biological sample image which is take when the biological sample is put on the diffusion unit.

9. The double-light cabinet as defined in claim 8, further comprising a comparison unit connected to the image capture unit to compare the biological sample image with the background image to form a detection image.

10. The double-light cabinet as defined in claim 1, further comprising a plurality of filter members respectively covering the first light sources.

11. The double-light cabinet as defined in claim 1, further comprising a plurality of filter members respectively covering the first light sources.

12. The double-light cabinet as defined in claim 1, wherein the dye is blue.

13. A double-light cabinet for testing a biological sample labeled with fluorochrome, comprising:

a case having a chamber;

a light unit, which is provided in the chamber of the case, having first light sources to emit a first light with a first wavelength and second light sources to emit a second light with a second wavelength, wherein the first light excites the fluorochrome, and the second light illuminates the biological sample; and a diffusion unit received in the chamber of the case, wherein the first light and the second light emit to the diffusion unit to form a first surface light and a second surface light and emit to the biological sample to excite the fluorochrome to generate a third light with a third wavelength;

wherein the diffusion unit has a plurality of recesses on at least an edge thereof to respectively receive the first light sources and the second light sources therein.

14. The double-light cabinet as defined in claim 13, wherein on sidewalls of the recesses receiving the first light sources are coated with dye.

15. The double-light cabinet as defined in claim 13, further comprising a plurality of filter members respectively covering the first light sources.

16. The double-light cabinet as defined in claim 14, wherein the dye is blue.

17. The double-light cabinet as defined in claim 13, further comprising an amber filter unit above the diffusion unit to filter the third light.

18. The double-light cabinet as defined in claim 17, further comprising an image capture unit above the amber filter unit to catch images through the amber filter unit, wherein the images include a background image which is taken when the biological sample is not put on the diffusion unit yet, and a biological sample image which is take when the biological sample is put on the diffusion unit.

19. The double-light cabinet as defined in claim 18, further comprising a comparison unit connected to the image capture unit to compare the biological sample image with the background image to form a detection image.

20. A double-light cabinet for testing a biological sample labeled with fluorochrome, comprising:

a case having a chamber;

a light unit, which is provided in the chamber of the case, having first light sources to emit a first light with a first wavelength and second light sources to emit a second light with a second wavelength, wherein the first light excites the fluorochrome, and the second light illuminates the biological sample; and a diffusion unit received in the chamber of the case, wherein the first light and the second light emit to the diffusion unit to form a first surface light and a second surface light and emit to the biological sample to excite the fluorochrome to generate a third light with a third wavelength;

wherein the diffusion unit has a plurality of recesses on at least an edge thereof to respectively receive the second light sources therein, and the first light sources are above the diffusion unit to directly emit the first light to the biological sample in a direction diverging from a normal of the diffusion unit.

21. The double-light cabinet as defined in claim 20, further comprising an amber filter unit above the diffusion unit to filter the third light.

22. The double-light cabinet as defined in claim 21, further comprising an image capture unit above the amber filter unit to catch images through the amber filter unit, wherein the images include a background image which is taken when the biological sample is not put on the diffusion unit yet, and a biological sample image which is take when the biological sample is put on the diffusion unit.

23. The double-light cabinet as defined in claim 21, further comprising a comparison unit connected to the image capture unit to compare the biological sample image with the background image to form a detection image.

* * * * *